United States Patent
Wang et al.

(10) Patent No.: US 12,064,666 B2
(45) Date of Patent: *Aug. 20, 2024

(54) PHYSICAL EXERCISE METHOD, CONTROLLER, AND SYSTEM

(71) Applicant: Telesair, Inc., Irvine, CA (US)

(72) Inventors: Qing Wang, Palo Alto, CA (US); Yong Liu, Orange, CA (US)

(73) Assignee: Telesair, Inc., Irvine, CA (US)

( * ) Notice: Subject to any disclaimer, the term of this patent is extended or adjusted under 35 U.S.C. 154(b) by 94 days.

This patent is subject to a terminal disclaimer.

(21) Appl. No.: 18/315,661

(22) Filed: May 11, 2023

(65) Prior Publication Data

US 2024/0189665 A1  Jun. 13, 2024

Related U.S. Application Data (63) Continuation of application No. 18/076,581, filed on Dec. 7, 2022, now Pat. No. 11,712,603.

(51) Int. Cl.
*A63B 24/00* (2006.01)
*A63B 71/06* (2006.01)

(52) U.S. Cl.
CPC ...... *A63B 24/0075* (2013.01); *A63B 71/0622* (2013.01); *A63B 2024/0068* (2013.01); *A63B 2071/0625* (2013.01); *A63B 2213/005* (2013.01); *A63B 2220/807* (2013.01); *A63B 2225/20* (2013.01); *A63B 2230/065* (2013.01); *A63B 2230/207* (2013.01)

(58) Field of Classification Search
CPC ............ A63B 24/0075; A63B 71/0622; A63B 2024/0068; A63B 2071/0625; A63B 2213/005; A63B 2220/807; A63B 2225/20; A63B 2230/065; A63B 2230/207

See application file for complete search history.

(56) References Cited

U.S. PATENT DOCUMENTS

| | | |
|---|---|---|
| 4,121,583 A | 10/1978 | Chen |
| 4,809,706 A | 3/1989 | Watson et al. |
| 5,207,623 A | 5/1993 | Tkatchouk et al. |
| 5,571,075 A | 11/1996 | Bullard |
| 5,984,873 A | 11/1999 | Crumb et al. |
| 6,131,569 A | 10/2000 | Schuster |
| 2002/0035927 A1 | 3/2002 | Kutt et al. |
| 2004/0006926 A1 | 1/2004 | Neeley et al. |
| 2005/0059530 A1 | 3/2005 | Chang |
| 2007/0023041 A1 | 2/2007 | Wang |
| 2008/0132383 A1 | 6/2008 | Einav et al. |
| 2011/0146687 A1 | 6/2011 | Fukushima |

(Continued)

FOREIGN PATENT DOCUMENTS

| | | |
|---|---|---|
| CN | 204910621 U | 12/2015 |
| CN | 110051989 A | 7/2019 |
| WO | 2016022974 A1 | 2/2016 |

*Primary Examiner* — Sundhara M Ganesan
(74) *Attorney, Agent, or Firm* — Maier & Maier, PLLC (57) ABSTRACT

A method for assisting a patient in physical rehabilitation, the method being executed by a controller, and the controller being configurable with at least one physical rehabilitation strategy and being communicatively connected with a respiratory device and an exercise device. The method includes controlling at least one of a device setting of the respiratory device and a device setting of the exercise device, based on a target physical rehabilitation strategy among the at least one physical rehabilitation strategy.

20 Claims, 4 Drawing Sheets

(56) References Cited

U.S. PATENT DOCUMENTS

| | | |
|---|---|---|
| 2012/0315614 A1 | 12/2012 | Krauza |
| 2013/0160767 A1 | 6/2013 | Abella |
| 2014/0107500 A1 | 4/2014 | Stamatopoulos et al. |
| 2015/0224270 A1 | 8/2015 | Frandson |
| 2015/0231443 A1 | 8/2015 | Halliday |
| 2015/0231447 A1 | 8/2015 | Hsu |
| 2015/0258560 A1 | 9/2015 | Ashby et al. |
| 2015/0327804 A1 | 11/2015 | Lefever et al. |
| 2016/0038071 A1 | 2/2016 | Williams et al. |
| 2016/0051847 A1 | 2/2016 | Zhang et al. |
| 2016/0317044 A1 | 11/2016 | Wu |
| 2017/0136205 A1 | 5/2017 | Rusher |
| 2018/0243608 A1 | 8/2018 | Jones et al. |
| 2018/0318642 A1 | 11/2018 | Lunz et al. |
| 2018/0339122 A1 | 11/2018 | Lunz et al. |
| 2020/0086074 A1 | 3/2020 | Rusher |
| 2020/0155898 A1 | 5/2020 | Kuronen et al. |
| 2021/0068668 A1 | 3/2021 | Slyusarenko et al. |
| 2022/0057092 A1 | 2/2022 | Mou et al. |
| 2022/0331659 A1 | 10/2022 | Chen et al. |
| 2022/0401672 A1 | 12/2022 | Trumbower et al. |

FIG. 1

Controlling at least one of a device setting of the respiratory device and a device setting of the exercise device, based on a target physical rehabilitation strategy among at least one physical rehabilitation strategy ⸺ S201

PHYSICAL EXERCISE METHOD, CONTROLLER, AND SYSTEM

This application is a continuation of U.S. patent application Ser. No. 18/076,581, filed on Dec. 7, 2022, which is hereby incorporated by reference in its entirety.

TECHNICAL FIELD

The present disclosure relates generally to the technical field of medical technology, and in particular, to a physical rehabilitation method and related products.

BACKGROUND

A respiratory disease may be caused by viruses, for example, the COVID-19 virus. Pulmonary fibrosis is a potential consequence of COVID-19 virus, leading to long-lasting respiratory problems and activity limitations, which may result in sever impacts in people's daily life.

Pulmonary rehabilitation is crucial for the recovering from pulmonary diseases such as those caused by COVID-19 viruses. Effective pulmonary rehabilitation solutions are an integral part of the treatment program of pulmonary diseases.

This background information is provided to reveal information believed by the applicant to be of possible relevance to the present disclosure. No admission is necessarily intended, nor should be construed, that any of the preceding information constitutes prior art against the present disclosure.

SUMMARY

The present disclosure provides a physical rehabilitation method and related products.

A first aspect of the present disclosure relates to a method for assisting a patient in physical rehabilitation, where the method is executed by a controller configurable with at least one physical rehabilitation strategy, the controller is communicatively connected with a respiratory device and an exercise device, and the method includes:
  controlling, based on a target physical rehabilitation strategy among the at least one physical rehabilitation strategy, at least one of a device setting of the respiratory device and a device setting of the exercise device.
In a possible implementation, the method further includes:
  receiving a physiological parameter of the patient transmitted by at least one measurement device associated with the patient; and
  adjusting, based on the physiological parameter and the target physical rehabilitation strategy, the at least one of the device setting of the respiratory device and the device setting of the exercise device.
In a possible implementation, the physiological parameter includes a heart rate of the patient;
  the adjusting, based on the physiological parameter and the target physical rehabilitation strategy, the at least one of the device setting of the respiratory device and the device setting of the exercise device includes:
  determining whether the heart rate of the patient exceeds an upper limit of a target heart rate range included in the target physical rehabilitation strategy; and
  in a case that the heart rate of the patient exceeds the upper limit of the target heart rate range, performing at least one of the following: modifying the device setting of the respiratory device to increase supplemental oxygen output by the respiratory device, or modifying the device setting of the exercise device to reduce an exercise intensity of the patient.

In a possible implementation, the physiological parameter includes SpO2 of the patient;
  the adjusting, based on the physiological parameter and the target physical rehabilitation strategy, the at least one of the device setting of the respiratory device and the device setting of the exercise device includes:
  determining whether a value of the SpO2 is lower than a first preset threshold included in the target physical rehabilitation strategy; and
  in a case that the value of the SpO2 is lower than the first preset threshold, performing at least one of the following: modifying the device setting of the respiratory device to increase supplemental oxygen output by the respiratory device, or modifying the device setting of the exercise device to reduce an exercise intensity of the patient.

In a possible implementation, in a case that the value of the SpO2 is lower than the first preset threshold, the method further includes:
  determining whether the value of the SpO2 is lower than a second preset threshold included in the target physical rehabilitation strategy, where the second preset threshold is lower than the first preset threshold; and
  outputting an alarm signal in a case that the SpO2 of the patient is lower than the second preset threshold.

In a possible implementation, the controlling, based on a target physical rehabilitation strategy among the at least one physical rehabilitation strategy, at least one of a device setting of the respiratory device and a device setting of the exercise device includes:
  determining whether the device setting of the respiratory device exceeds a third preset threshold, where the third preset threshold is included in the target physical rehabilitation strategy; and
  modifying the device setting of the exercise device to reduce an exercise intensity of the patient, in a case that the device setting of the respiratory device exceeds the third preset threshold.

In a possible implementation, the method further includes:
  setting the target physical rehabilitation strategy based on at least one input of a user, where the at least one input corresponds to a rehabilitation decision determined by the user.

In a possible implementation, before the setting the target physical rehabilitation strategy based on at least one input of a user, the method further includes:
  receiving authentication information input by the user; and
  determining, according to the authentication information, whether the user has an authority for accessing the at least one physical rehabilitation strategy.

In a possible implementation, the method further includes:
  outputting a reminder signal at a start time of the physical rehabilitation, where the start time is included in the target physical rehabilitation strategy, and the reminder signal is used to remind the patient that it is time for physical rehabilitation.

In a possible implementation, the method further includes:
  receiving a stop instruction, where the stop instruction is input by the patient by pressing a stop button on the controller, or the stop instruction is transmitted by the user through a remote terminal; and controlling the exercise device to stop running.

In a possible implementation, the method further includes:

outputting an exercise guidance for the physical rehabilitation through at least one of a display screen and a speaker, where the display and the speaker are communicatively connected with the controller, and the exercise guidance is included in the target physical rehabilitation strategy and is used to provide a guidance for exercise to the patient.

In a possible implementation, the method further includes:

receiving an image of the patient from a camera communicatively connected with the controller and disposed in front of the patient; and transmitting the image of the patient to a remote terminal.

A second aspect of the present disclosure relates to an apparatus for assisting a patient in physical rehabilitation, where the apparatus is configurable with at least one physical rehabilitation strategy and communicatively connected with a respiratory device and an exercise device, and the apparatus includes:

a controlling module, configured to control at least one of a device setting of the respiratory device and a device setting of the exercise device, based on a target physical rehabilitation strategy among the at least one physical rehabilitation strategy.

In a possible implementation, the apparatus further includes:

a receiving module, configured to receive a physiological parameter of the patient transmitted by at least one measurement device associated with the patient; and an adjusting module, configured to adjust the at least one of the device setting of the respiratory device and the device setting of the exercise device, based on the physiological parameter and the target physical rehabilitation strategy.

In a possible implementation, the physiological parameter includes a heart rate of the patient, and the adjusting module includes:

a first determining unit, configured to determine whether the heart rate of the patient exceeds an upper limit of a target heart rate range included in the target physical rehabilitation strategy; and a first adjusting unit, configured to: in a case that the heart rate of the patient exceeds the upper limit of the target heart rate range, perform at least one of the following: modifying the device setting of the respiratory device to increase supplemental oxygen output by the respiratory device, or modifying the device setting of the exercise device to reduce an exercise intensity of the patient.

In a possible implementation, the physiological parameter includes SpO2 of the patient, and the adjusting module includes:

a second determining unit, configured to determine whether a value of the SpO2 is lower than a first preset threshold included in the target physical rehabilitation strategy; and a second adjusting unit, configured to: in a case that the value of the SpO2 is lower than the first preset threshold, perform at least one of the following: modifying the device setting of the respiratory device to increase supplemental oxygen output by the respiratory device, or modifying the device setting of the exercise device to reduce an exercise intensity of the patient.

In a possible implementation, the second determining unit is further configured to: in a case that the value of the SpO2 is lower than the first preset threshold, determine whether the value of the SpO2 is lower than a second preset threshold included in the target physical rehabilitation strategy, where the second preset threshold is lower than the first preset threshold;

the apparatus further includes: a first outputting module, configured to output an alarm signal in a case that the SpO2 of the patient is lower than the second preset threshold.

In a possible implementation, the controlling module includes:

a third determining unit, configured to determine whether the device setting of the respiratory device exceeds a third preset threshold, where the third preset threshold is included in the target physical rehabilitation strategy; and a third adjusting unit, configured to modify the device setting of the exercise device to reduce an exercise intensity of the patient, in a case that the device setting of the respiratory device exceeds the third preset threshold.

In a possible implementation, the apparatus further includes:

a setting module, configured to set the target physical rehabilitation strategy based on at least one input of a user, where the at least one input corresponds to a rehabilitation decision determined by the user.

In a possible implementation, the apparatus further includes:

a second receiving module, configured to receive authentication information input by the user; and a determining module, configured to determine, according to the authentication information, whether the user has an authority for accessing the at least one physical rehabilitation strategy.

In a possible implementation, the apparatus further includes:

a second outputting module, configured to output a reminder signal at a start time of the physical rehabilitation, where the start time is included in the target physical rehabilitation strategy, and the reminder signal is used to remind the patient that it is time for physical rehabilitation.

In a possible implementation, the apparatus further includes:

a third receiving module, configured to receive a stop instruction, where the stop instruction is input by the patient by pressing a stop button on the controller, or the stop instruction is transmitted by the user through a remote terminal; and the controlling module is configured to control the exercise device to stop running.

In a possible implementation, the apparatus further includes:

a third outputting module, configured to output an exercise guidance for the physical rehabilitation through at least one of a display screen and a speaker, where the display and the speaker are communicatively connected with the controller, and the exercise guidance is included in the target physical rehabilitation strategy and is used to provide a guidance for exercise to the patient.

In a possible implementation, the apparatus further includes:
- a fourth receiving module, configured to receive an image of the patient from a camera communicatively connected with the controller and disposed in front of the patient; and
- a transmitting module, configured to transmit the image of the patient to a remote terminal.

A third aspect of the present disclosure relates to a controller configurable with at least one physical rehabilitation strategy and communicatively connected with a respiratory device and an exercise device, the controller including:
- at least one processor; and
- a memory communicatively connected with the at least one processor;
- where the memory stores instructions executable by the at least one processor, and the instructions, when executed by the at least one processor, cause the at least one processor to:
  - control at least one of a device setting of the respiratory device and a device setting of the exercise device, based on a target physical rehabilitation strategy among the at least one physical rehabilitation strategy.

A fourth aspect of the present disclosure relates to a system for assisting a patient in physical rehabilitation, including a controller configurable with at least one physical rehabilitation strategy and communicatively connected with a respiratory device and an exercise device;
- where the controller includes at least one processor, and a memory communicatively connected with the at least one processor, the memory stores instructions executable by the at least one processor, and the instructions, when executed by the at least one processor, cause the at least one processor to:
  - control at least one of a device setting of the respiratory device and a device setting of the exercise device, based on a target physical rehabilitation strategy among the at least one physical rehabilitation strategy.

In a possible implementation, the instructions, when executed by the at least one processor, cause the at least one processor to:
- receive a physiological parameter of the patient transmitted by at least one measurement device associated with the patient; and
- adjust, based on the physiological parameter and the target physical rehabilitation strategy, the at least one of the device setting of the respiratory device and the device setting of the exercise device.

In a possible implementation, the instructions, when executed by the at least one processor, cause the at least one processor to:
- set the target physical rehabilitation strategy based on at least one input of a user, where the at least one input corresponds to a rehabilitation decision determined by the user.

In a possible implementation, the instructions, when executed by the at least one processor, cause the at least one processor to:
- receive authentication information input by the user; and
- determine, according to the authentication information, whether the user has an authority for accessing the at least one physical rehabilitation strategy.

In a possible implementation, the instructions, when executed by the at least one processor, cause the at least one processor to:
- output a reminder signal at a start time of the physical rehabilitation, where the start time of the physical rehabilitation is included in the target physical rehabilitation strategy, and the reminder signal is used to remind the patient that it is time for physical rehabilitation.

In a possible implementation, the system further includes a display screen and a speaker communicatively connected with the controller, and the instructions, when executed by the at least one processor, cause the at least one processor to:
- output an exercise guidance for the physical rehabilitation through at least one of the display screen and the speaker, where the exercise guidance is included in the target physical rehabilitation strategy and is used to provide a guidance for exercise to the patient.

In a possible implementation, the system further includes a camera communicatively connected with the controller and disposed in front of the patient, and the instructions, when executed by the at least one processor, cause the at least one processor to:
- receive an image of the patient from the camera; and
- transmit the image of the patient to a remote terminal.

A fifth aspect of the present disclosure relates to a non-transitory computer readable storage medium, storing thereon computer executable instructions which, when being executed by a controller configurable with at least one physical rehabilitation strategy and communicatively connected with a respiratory device and an exercise device, implement:
- control at least one of a device setting of the respiratory device and a device setting of the exercise device, based on a target physical rehabilitation strategy among the at least one physical rehabilitation strategy.

DETAILED DESCRIPTION OF EMBODIMENTS

In the following description, reference is made to the accompanying figures, which form part of the disclosure, and which show, by way of illustration, specific aspects of embodiments of the present disclosure or specific aspects in which embodiments of the present disclosure may be used. It is understood that embodiments of the present disclosure may be used in other aspects and include structural or logical changes not depicted in the figures. The following detailed description, therefore, is not to be taken in a limiting sense, and the scope of the present disclosure is defined by the appended claims.

For instance, it is understood that a disclosure in connection with a described method may also hold true for a corresponding device or system configured to perform the method and vice versa. For example, if one or a plurality of specific method steps are described, a corresponding device may include one or a plurality of units, e.g. functional units, to perform the described one or plurality of method steps (e.g. one unit performing the one or plurality of steps, or a plurality of units each performing one or more of the plurality of steps), even if such one or more units are not explicitly described or illustrated in the figures. On the other hand, for example, if a specific apparatus is described based on one or a plurality of units, e.g. functional units, a corresponding method may include one step to perform the functionality of the one or plurality of units (e.g. one step performing the functionality of the one or plurality of units, or a plurality of steps each performing the functionality of one or more of the plurality of units), even if such one or plurality of steps are not explicitly described or illustrated in the figures. Further, it is understood that the features of the various exemplary embodiments and/or aspects described herein may be combined with each other, unless specifically noted otherwise.

In the embodiments of the present disclosure, expressions such as "exemplary" or "for example" are used to indicate illustration of an example or an instance. In the embodiments of the present disclosure, any embodiment or design scheme described as "exemplary" or "for example" should not be interpreted as preferred or advantageous over other embodiments or design schemes. In particular, the use of "exemplary" or "for example" is aimed at presenting related concepts in a specific manner.

The term "patient" refers to a person who is the subject to which the methods and/or apparatuses described herein are helping in physical rehabilitation.

The term "physiological parameter" refers to a parameter obtained passively or actively from the patient that is indicative of present physiological state of the patient. The example embodiments discussed herein discuss various examples of physiological parameter that may be employed, however, it is to be appreciated that other physiological parameter may be employed without varying from the scope of the present disclosure.

The term "controller" shall mean a number of programmable analog and/or digital devices (including an associated memory part or portion) that can store, retrieve, execute and process data (e.g., software routines and/or information used by such routines), including, without limitation, a field programmable gate array (FPGA), a complex programmable logic device (CPLD), a programmable system on a chip (PSOC), an application specific integrated circuit (ASIC), a microprocessor, a microcontroller, a programmable logic controller, or any other suitable processing device or apparatus. The memory portion can be any one or more of a variety of types of internal and/or external storage media such as, without limitation, RAM, ROM, EPROM(s), EEPROM(s), FLASH, and the like that provide a storage register, i.e., a non-transitory machine readable medium, for data and program code storage such as in the fashion of an internal storage area of a computer, and can be volatile memory or nonvolatile memory.

For many patients diagnosed with chronic lung conditions such as chronic obstructive pulmonary disease (COPD), and those patients with lung transplant, patients with lung cancer, and patients with conditions such as asthma, pulmonary hypertension, and cystic fibrosis, attending a pulmonary rehabilitation (PR) program can be a lifesaver.

Pulmonary rehabilitation is a program designed for people who have chronic lung disease. Its primary goal is to enable people to achieve and maintain their maximum level of independence and functioning. Pulmonary rehabilitation applies supervised exercise, education, support, and behavioral intervention to improve how people with chronic lung disease function in daily life. Pulmonary rehabilitation can help people manage their symptoms, complications, oxygen and medications, reduce shortness of breath, increase exercise tolerance, enhance a sense of well-being, reduce hospitalizations, and most importantly, breathe better and improve quality of life.

Trained respiratory therapists, physical therapists, nurses and doctors are often required to manage the pulmonary rehabilitation process, and ensure proper protocols are followed, making pulmonary rehabilitation a resource intensive activity. Thus, in terms of treatment of patients with chronic lung conditions, providing effective and efficient pulmonary rehabilitation solutions are significant to reduce the workload of the medical workers.

A method for assisting a patient in physical rehabilitation is described in the present disclosure. An aim of the solution provided in the present disclosure is to enable automatic, and semi-automatic control of the devices used during physical rehabilitation procedure, which helps reduce workload of the medical workers, minimize operational mistakes, and enhance therapeutic effectiveness. This disclosure may also help patients to conduct rehabilitation exercises at home, with no supervision of professional therapists, or remote supervision of the professional therapists.

Figure 1:
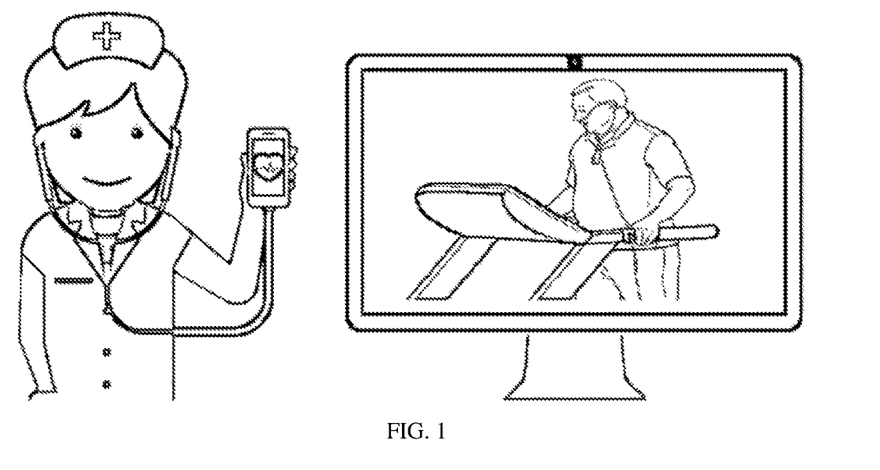
FIG. 1 is a schematic diagram of an application scenario of a method for assisting a patient in physical rehabilitation according to an embodiment of the present disclosure.

FIG. 1 is a schematic diagram of an application scenario of a method for assisting a patient in physical rehabilitation according to an embodiment of the present disclosure. As shown in FIG. 1, a patient is in physical rehabilitation under assistance of a respiratory device and an exercise device. The patient may be a person with a chronic lung disease such as COPD, and accordingly, the method is for pulmonary rehabilitation. The patient may also be a person with other disease that needs a rehabilitation procedure. A controller (not shown) configurable with at least one physical rehabilitation strategy may, based on a target physical rehabilitation strategy among the at least one physical rehabilitation strategy, control at least one of a device setting of the respiratory device and a device setting of the exercise device. A user (e.g. a respiratory therapist, a doctor or a nurse) may also control the device setting of the respiratory device or the device setting of the exercise device. An efficient method for assisting a patient in physical rehabilitation is achieved.

It should be noted that the user, i.e. the caregiver, may be with the patient, for example, when the patient undergoes physical rehabilitation at a rehabilitation medical facility. In another case, a user in a hospital or a rehabilitation medical facility can remotely monitor and control the respiratory device and the exercise device through a remote terminal while a patient undergoes physical rehabilitation in the same hospital or rehabilitation facility. In yet another case, a user in a hospital or a rehabilitation medical facility can remotely control the respiratory device and the exercise device through a remote terminal while a patient undergoes physical rehabilitation at home.

It should be understood that, FIG. 1 is merely a logical schematic diagram, and in a practical application scenario, the function components may be implemented in various forms. For example, the controller may be an independent handheld device, and a user can specify on the handheld device the device setting of the exercise device and the device setting of the respiratory device. In another example, the controller may be integrated into the exercise device as a hardware/software/firmware unit of the exercise device, and the user can specify the device setting of the exercise device and the device setting of the respiratory device through a touch screen of the exercise device, where the touch screen is communicatively connected with the controller.

The application scenario of the embodiment of the present disclosure described above is only illustrative, and other application scenarios may also be employed, which is not limited in the embodiments of the present disclosure.

Figure 2:
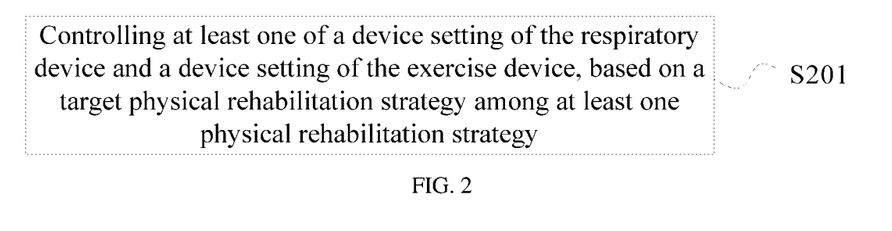
FIG. 2 is a flowchart of a method for assisting a patient in physical rehabilitation according to an embodiment of the present disclosure.

FIG. 2 is a flowchart of a method for assisting a patient in physical rehabilitation according to an embodiment of the present disclosure. The method may be executed by a controller communicatively connected with a respiratory device and an exercise device, and the controller is configurable with at least one physical rehabilitation strategy, that is, at least one physical rehabilitation strategy can be configured in the controller by a user (e.g., a respiratory therapist) of the controller, the controller simply acts as a tool for automatically implementing the physical rehabilitation strategies configured by the user. More specifically, there may be different physical rehabilitation strategies for different patients, and there may also be different physical rehabilitation strategies for different respiratory devices and different exercise devices. A user may specify a physical rehabilitation strategy for a specific patient or a kind of patients, and input the physical rehabilitation strategy into the controller for assisting a patient in physical rehabilitation. Alternatively, a user may also specify various different physical rehabilitation strategies and input them into the controller, and when it is required to assist a patient in physical rehabilitation, a respiratory therapist may select one of the physical rehabilitation strategies according to the condition of the patient, such as COPD, lung transplant, lung cancer, or other conditions. The controller may include a rehabilitation program specific to a patient, associated to a patient identification code.

The method for assisting a patient in physical rehabilitation includes: step 201, controlling at least one of a device setting of the respiratory device and a device setting of the exercise device, based on a target physical rehabilitation strategy among at least one physical rehabilitation strategy.

The respiratory device provides supplemental oxygen to the patient due to exercise-induced oxygen desaturation during a physical rehabilitation procedure. Supplemental oxygen during rehabilitation exercise reduces minute ventilation at equivalent work rates and delays the onset of dynamic hyperinflation and thus augments exercise capacity. The exercise device provides support for exercise of the patient.

The above step 201 may include: determining whether the device setting of the respiratory device exceeds a third preset threshold, where the third preset threshold is included in the target physical rehabilitation strategy; and modifying the device setting of the exercise device to reduce an exercise intensity of the patient, in a case that the device setting of the respiratory device exceeds the third preset threshold.

In a specific implementation, the respiratory device may be a HFNC (high flow nasal cannula), and the exercise device may be a treadmill. The device setting of the respiratory device may include a flow rate of the HFNC and an FiO2 (Fraction of Inspired Oxygen, the concentration of oxygen in the gas mixture) of the HFNC, and the device setting of the exercise device may include a speed of the treadmill and a slope of the treadmill.

The above step 201 may include: determining whether the flow rate of the HFNC is greater than a third preset threshold or the FiO2 of the HFNC is greater than a fourth preset threshold, where the third preset threshold and the fourth preset threshold are included in the target physical rehabilitation strategy; and reducing at least one of the speed of the treadmill and the slope of the treadmill in a case that the flow rate of the HFNC is greater than the third preset threshold or the FiO2 of the HFNC is greater than the fourth preset threshold. The third preset threshold and the fourth preset threshold may be set according to actual needs.

It should be noted that the respiratory device may also be other devices capable of providing supplemental oxygen during a physical rehabilitation procedure, such as an oxygen concentrator or a non-invasive ventilator (NIV), and the device setting of the respiratory device may be a flow rate of the oxygen concentrator or a pressure of the NIV, which is not limited in the present disclosure, as long as it can increase exercise tolerance, reduce exercise induced desaturation and improve the outcome of the exercise. In addition, the exercise device may also be a bicycle ergometer or a stepper, and the device setting of the exercise device may be a resistance or a speed of the bicycle ergometer or the stepper, which is not limited in the present disclosure.

In an implementation, the controller may receive authentication information input by a user (e.g. a respiratory therapist, a doctor, or a nurse) and determine, according to the authentication information, whether the user has an authority for accessing the at least one physical rehabilitation strategy associated with the controller. For example, there may be different IDs (e.g. the names of medical workers) and corresponding passwords preset for the medical workers, and a medical worker may input his own ID and password, or use biometric authentication (e.g. fingerprint), to authenticate that he has the authority for accessing the physical rehabilitation strategies in the controller, thereby improving the security of the physical rehabilitation strategies.

In a case that the authentication is successful, i.e. the user has the authority for accessing the physical rehabilitation strategies in the controller, the user can select a physical rehabilitation strategy according to the condition of a patient from the physical rehabilitation strategies. The user can also set up or modify the selected physical rehabilitation strategy, for example, set up or modify a threshold at which the controller output an alarm signal to inform the user the critical adverse condition of SpO2 (Oxygen Saturation Level, a percentage of oxygen in blood), breath rate, or heart rate of the patient.

In an implementation, the controller may set the target physical rehabilitation strategy based on at least one input of a user, where the at least one input corresponds to a rehabilitation decision determined by the user.

Specifically, the user may import the at least one input through a remote terminal and transmit the at least one input to the controller, and accordingly, the controller sets the target physical rehabilitation strategy based on the at least one input. The user may be a respiratory therapist, a doctor or a nurse, and the at least one input corresponds to a rehabilitation decision determined by the respiratory therapist, the doctor or the nurse. The at least one input includes, but not limited to, a starting flow rate of a HFNC, a starting FiO2 of the HFNC, a time interval the flow rate or the FiO2 is adjusted, a step size the flow rate or the FiO2 is adjusted, a speed of a treadmill, a slope of a treadmill, a threshold at which the controller output an alarm signal to inform the user the critical adverse condition of the SpO2, breath rate, or heart rate of the patient, a time duration for one time physical rehabilitation, etc. In an example, the flow rate may increase 1 lpm every 5 minutes of exercise on a treadmill. In another example, the FiO2 may increase 1% every 10 minutes of exercise on a treadmill.

In an implementation, the controller may receive a physiological parameter of the patient transmitted by at least one measurement device associated with the patient. The physiological parameter may include at least one of SpO2 and a heart rate, and the at least one measurement device may include at least one of an oximeter and a wearable device. The SpO2 may be transmitted to the controller by the oximeter associated with the patient, and the heart rate may be transmitted to the controller by the wearable device associated with the patient.

For example, an oximeter and a wearable device may respectively be connected to the patient and obtain SpO2 and the heart rate of the patient, respectively. The oximeter and the wearable device may, through a wired or wireless manner, transmit the obtained SpO2 and the obtained heart rate of the patient to the controller, respectively. The wearable device may be any existing device that can measure the heart rate of the patient, such as a smartwatch. Correspondingly, the controller receives the SpO2 and the heart rate of the patient transmitted by the oximeter and the wearable device.

It should be understood that the physiological parameter may include other indicators of the patient, such as a breath rate, and the controller may receive those other indicators from corresponding measurement devices, which is not limited in the embodiment of the present disclosure.

Based on the physiological parameter and the target physical rehabilitation strategy, the controller may adjust the at least one of the device setting of the respiratory device and the device setting of the exercise device.

For example, after receiving the physiological parameter such as the heart rate of the patient, the controller may determine whether the heart rate of the patient exceeds an upper limit of a target heart rate range included in the target physical rehabilitation strategy. In a case that the heart rate of the patient exceeds the upper limit of the target heart rate range, the controller may modify the device setting of the respiratory device to increase supplemental oxygen output by the respiratory device, or modify the device setting of the exercise device to reduce an exercise intensity of the patient. For example, the controller may increase a flow rate or a FiO2 of the HFNC, and the controller may also reduce a speed or a slope of the treadmill.

The table below shows different target heart rate (HR) zones (ranges) and different average maximum heart rate related to different age groups, and the table may be included in the physical rehabilitation strategies and stored in the controller. Specifically, one age group may correspond to one physical rehabilitation strategy, and a user such as a professional therapist may select the target physical rehabilitation strategy based on the age of the patient. When the real-time heart rate is approaching or arriving at the upper limit of the target heart rate zone, the controller will reduce speed and/or slope to the treadmill. The speed can be reduced to zero to stop the treadmill. In another embodiment, when the real-time heart rate is approaching or arriving at the upper limit of the target heart rate zone, the controller may increase the flow rate of the respiratory device (e.g. HFNC). In another embodiment, when the real-time heart rate is approaching or arriving at the upper limit of the target heart rate zone, the controller may increase the FiO2 of the respiratory device. In another embodiment, when the real-time heart rate is approaching or arriving at the upper limit of the target heart rate zone, the controller may output a yellow alert. By implementing the method provided in the embodiments of the present disclosure, the recovery time can be shortened, and the recovery speed can be improved.

| Age | Target HR Zone 50-85% | Average Maximum Heart Rate, 100% |
|---|---|---|
| 20 years | 100-170 beats per minute (bpm) | 200 bpm |
| 30 years | 95-162 bpm | 190 bpm |
| 35 years | 93-157 bpm | 185 bpm |
| 40 years | 90-153 bpm | 180 bpm |
| 45 years | 88-149 bpm | 175 bpm |
| 50 years | 85-145 bpm | 170 bpm |
| 55 years | 83-140 bpm | 165 bpm |
| 60 years | 80-136 bpm | 160 bpm |
| 65 years | 78-132 bpm | 155 bpm |
| 70 years | 75-128 bpm | 150 bpm |

In another example, after receiving the physiological parameter such as SpO2 of the patient, the controller may determine whether the value of the SpO2 is lower than a first preset threshold (e.g. 93%) included in the target physical rehabilitation strategy. In a case that the value of the SpO2 is lower than the first preset threshold, the controller may modify the device setting of the respiratory device to increase supplemental oxygen output by the respiratory device, or modify the device setting of the exercise device to reduce an exercise intensity of the patient. For example, the controller may increase the flow rate or the FiO2 of the HFNC, and the controller may also reduce the speed or the slope of the treadmill. In an implementation, the controller may send a notification of the changes on HFNC or the treadmill to a terminal remotely located with the professional therapist.

In a case that the value of the SpO2 is lower than the first preset threshold, the controller may further determine whether the value of the SpO2 is lower than a second preset threshold (e.g. 90%) included in the target physical rehabilitation strategy. In a case that the SpO2 of the patient is lower than the second preset threshold, the controller may output an alarm signal to notify the user (e.g. the respiratory therapist, the doctor, or the nurse) the critical adverse condition of the SpO2 of the patient. The alarm signal may be a flashing light or a bell communicatively connected to the controller. The alarm signal may also be a voice notification which is transmitted to a remote terminal or APP integrated therein or other devices that may be tracking the physiological parameter of the patient.

In another example, the controller may adjust the device setting of the respiratory device and the device setting of the exercise device based on the progress of patient's condition. The adjustments may be the frequency of exercises each day, the duration and intensity of exercises, or a combination of frequency, duration, and intensity.

In a possible implementation, the controller may evaluate the effectiveness of a physical rehabilitation strategy (protocol). For example, the controller may measure the duration of the physical rehabilitation for the patient to fully recover. In another example, the controller may use artificial intelligence to modify a physical rehabilitation strategy for optimizing a patient's recovery. The specific algorithm of using artificial intelligence to modify the physical rehabilitation strategy may be an algorithm commonly used in prior art, which is not limited in the embodiment of the present disclosure.

In an implementation, the controller may remind the patient in a case that the patient forgets to do physical rehabilitation. Specifically, the controller may output a reminder signal at a start time of the physical rehabilitation (e.g. 9:00 AM), where the start time is included in the target physical rehabilitation strategy, and the reminder signal is used to remind the patient that it is time for physical rehabilitation.

In an implementation, when there is a need to stop the exercise device, the patient or the user may directly stop the exercise device during physical rehabilitation. For example, the patient may have a need to go to the bathroom during physical rehabilitation, at this time the patient may stop the exercise device by pressing a STOP button on the controller. In another example, when the user (e.g. the respiratory therapist, the doctor, or the nurse) determines that it is not suitable for the patient to continue the physical rehabilitation based on the condition of the patient, e.g. the SpO2 of the patient is too low, the user may stop the exercise device by transmitting a stop instruction through a remote terminal. Accordingly, the controller may receive the stop instruction from the patient or the user, and control the exercise device to stop in a controlled manner.

In an implementation, a display screen and a speaker in the vicinity of the exercise location may be communicatively connected with the controller. The controller may, through at least one of the display screen and the speaker, output exercise guidance for the physical rehabilitation, where the exercise guidance is included in the target physical rehabilitation strategy and is used to provide exercise guidance to the patient.

The exercise guidance may contain a warm-up phase guidance, a conditioning phase guidance, and a cool-down phase guidance. In an example, the exercise guidance may include several items for the physical rehabilitation and the items may be listed in the display screen in sequence. The patient may click from the first item to the last item one by one and do physical rehabilitation according to each item. The items may include walking, running corresponding to different speeds and different slopes of a treadmill, etc. In another example, the exercise guidance may also be provided to the patient through the speaker.

In an implementation, there may be a camera or an image sensor communicatively connected with the controller and disposed in front of the patient, which can take an image of the patient and transmit the image to the controller. The image of the patient indicates the current state of the patient. The controller may receive the image of the patient from the camera and transmit the image of the patient to a remote terminal or an APP integrated therein, or other devices that may be tracking the physiological state of the patient. The camera may also transmit the image of the patient to a remote terminal or an APP integrated therein, or other devices that may be tracking the physiological state of the patient.

In an implementation, an audio device may be communicatively connected with the controller or integrated in the controller, which can achieve bidirectional audio capability with another audio device integrated in a remote terminal, to enable audio communication between the patient and the user (caregiver) such as a respiratory therapist, a doctor or a nurse.

In an implementation, a smart phone or a personal assistant device (PDA) may be wirelessly connected with the controller and can communicate with the controller. The patient or the user (e.g. the respiratory therapist, doctor, or nurse) may control the device setting of the respiratory device and the device setting of the exercise device through the smart phone or the PDA, or an APP integrated therein.

Figure 3:
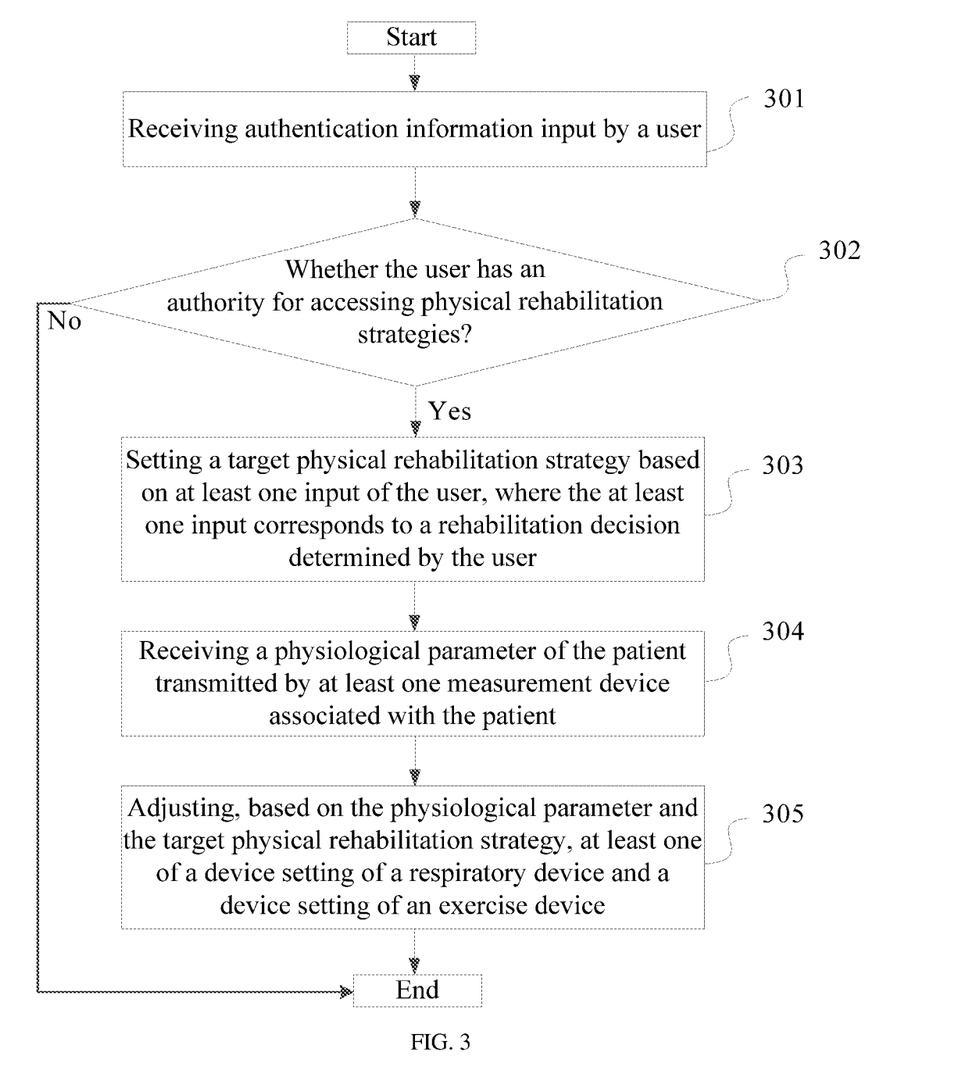
FIG. 3 is a flowchart of a method for assisting a patient in physical rehabilitation according to an embodiment of the present disclosure.

FIG. 3 is a flowchart of a method for assisting a patient in physical rehabilitation according to an embodiment of the present disclosure. As shown in FIG. 3, the method includes the following steps.

Step 301, receiving authentication information input by a user.

Step 302, determining whether the user has an authority for accessing the physical rehabilitation strategies, according to the authentication information.

Step 303, setting a target physical rehabilitation strategy based on at least one input of the user, where the at least one input corresponds to a rehabilitation decision determined by the user.

Step 304, receiving a physiological parameter of the patient transmitted by at least one measurement device associated with the patient.

Step 305, adjusting, based on the physiological parameter and the target physical rehabilitation strategy, at least one of a device setting of a respiratory device and a device setting of an exercise device.

The specific details of the embodiment can refer to the description described above, and the implementation principle and technical effects thereof are similar, which are not described herein.

Figure 4:
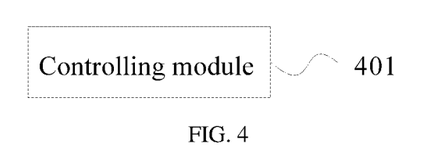
FIG. 4 is a schematic block diagram of an apparatus for assisting a patient in physical rehabilitation according to an embodiment of the present disclosure.

FIG. 4 is a schematic block diagram of an apparatus for assisting a patient in physical rehabilitation according to an embodiment of the present disclosure. The apparatus is configurable with at least one physical rehabilitation strategy and communicatively connected with a respiratory device and an exercise device. As shown in FIG. 4, the apparatus includes: a controlling module 401, configured to control at least one of a device setting of the respiratory device and a device setting of the exercise device, based on a target physical rehabilitation strategy among the at least one physical rehabilitation strategy.

In a possible implementation, the apparatus further includes: a receiving module, configured to receive a physiological parameter of the patient transmitted by at least one measurement device associated with the patient; and an adjusting module, configured to adjust the at least one of the device setting of the respiratory device and the device setting of the exercise device, based on the physiological parameter and the target physical rehabilitation strategy.

In a possible implementation, the physiological parameter includes a heart rate of the patient and the adjusting module includes: a first determining unit, configured to determine whether the heart rate of the patient exceeds an upper limit of a target heart rate range included in the target physical rehabilitation strategy; and a first adjusting unit, configured to: in a case that the heart rate of the patient exceeds the upper limit of the target heart rate range, perform at least one of the following: modifying the device setting of the respiratory device to increase supplemental oxygen output by the respiratory device, or modifying the device setting of the exercise device to reduce an exercise intensity of the patient.

In a possible implementation, the physiological parameter includes SpO2 of the patient, and the adjusting module includes: a second determining unit, configured to determine whether a value of the SpO2 is lower than a first preset threshold included in the target physical rehabilitation strategy; and a second adjusting unit, configured to: in a case that the value of the SpO2 is lower than the first preset threshold, perform at least one of the following: modifying the device setting of the respiratory device to increase supplemental oxygen output by the respiratory device, or modifying the device setting of the exercise device to reduce an exercise intensity of the patient.

In a possible implementation, the second determining unit is further configured to: in a case that the value of the SpO2 is lower than the first preset threshold, determine whether the value of the SpO2 is lower than a second preset threshold included in the target physical rehabilitation strategy, where the second preset threshold is lower than the first preset threshold. The apparatus further includes: a first outputting module, configured to output an alarm signal in a case that the SpO2 of the patient is lower than the second preset threshold.

In a possible implementation, the controlling module includes: a third determining unit, configured to determine whether the device setting of the respiratory device exceeds a third preset threshold, where the third preset threshold is included in the target physical rehabilitation strategy; and a third adjusting unit, configured to modify the device setting of the exercise device to reduce an exercise intensity of the patient, in a case that the device setting of the respiratory device exceeds the third preset threshold.

In a possible implementation, the apparatus further includes: a setting module, configured to set the target physical rehabilitation strategy based on at least one input of a user, where the at least one input corresponds to a rehabilitation decision determined by the user.

In a possible implementation, the apparatus further includes: a second receiving module, configured to receive authentication information input by the user; and a determining module, configured to determine, according to the authentication information, whether the user has an authority for accessing the at least one physical rehabilitation strategy.

In a possible implementation, the apparatus further includes: a second outputting module, configured to output a reminder signal at a start time of the physical rehabilitation, where the start time is included in the target physical rehabilitation strategy, and the reminder signal is used to remind the patient that it is time for physical rehabilitation.

In a possible implementation, the apparatus further includes: a third receiving module, configured to receive a stop instruction, where the stop instruction is input by the patient by pressing a stop button on the controller, or the stop instruction is transmitted by the user through a remote terminal; and the controlling module is configured to control the exercise device to stop running.

In a possible implementation, the apparatus further includes: a third outputting module, configured to output an exercise guidance for the physical rehabilitation through at least one of a display screen and a speaker, where the display and the speaker are located in the vicinity of the exercise device, and communicatively connected with the controller, and the exercise guidance is included in the target physical rehabilitation strategy and is used to provide a guidance for exercise to the patient.

In a possible implementation, the apparatus further includes: a fourth receiving module, configured to receive an image of the patient from a camera communicatively connected with the controller and disposed in front of the patient; and a transmitting module, configured to transmit the image of the patient to a remote terminal.

The apparatus for assisting a patient in physical rehabilitation in the embodiment may perform the technical solutions of the method embodiments shown in FIG. 2 and FIG. 3, and the implementation principle and technical effects thereof are similar, and details are not described herein.

Figure 5:
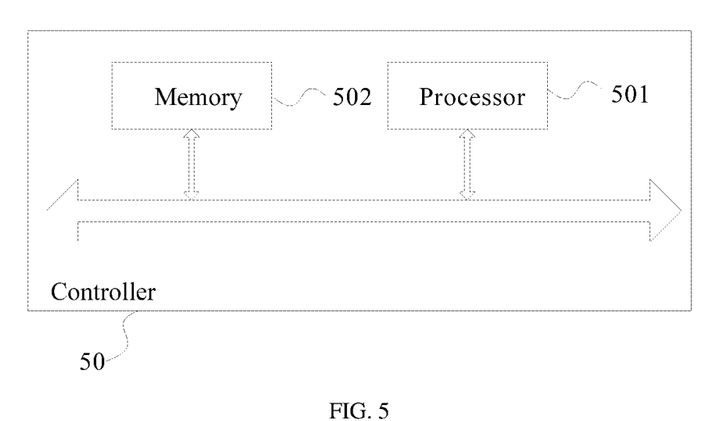
FIG. 5 is a schematic structural diagram of a controller according to an embodiment of the present disclosure.

FIG. 5 is a schematic structural diagram of a controller 50 according to an embodiment of the present disclosure. As shown in FIG. 5, the controller in the embodiment includes: at least one processor 501; and a memory 502 communicatively connected with the at least one processor 501.

The memory 502 stores instructions executable by the at least one processor 501, and the instructions, when executed by the at least one processor 501, cause the at least one processor 501 to implement the methods for assisting a patient in physical rehabilitation according to the embodiments of the present disclosure.

The related description can be understood by referring to the related descriptions corresponding to FIG. 2 and FIG. 3, and details are not described herein.

Figure 6:
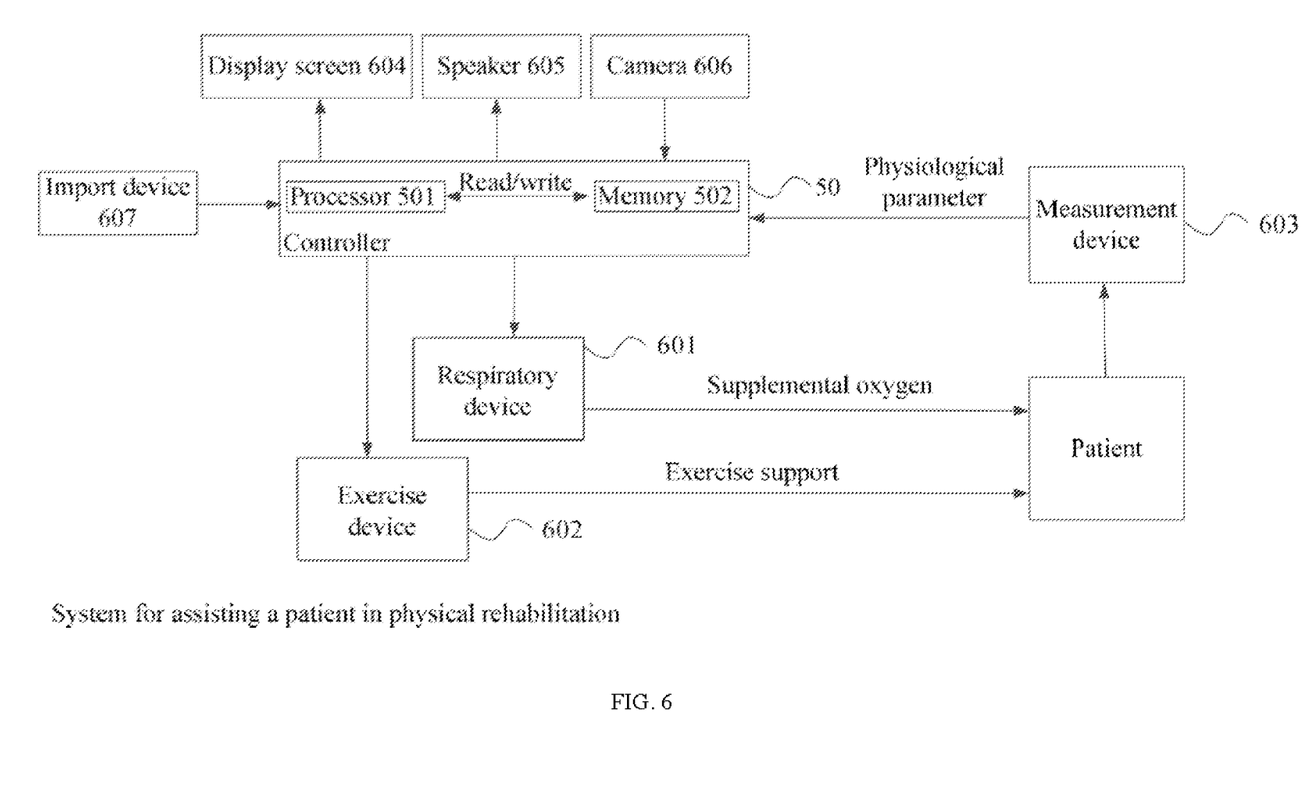
FIG. 6 is a schematic structural diagram of a system for assisting a patient in physical rehabilitation according to an embodiment of the present disclosure.

The present disclosure further provides a system for assisting a patient in physical rehabilitation, including a controller 50 configurable with at least one physical rehabilitation strategy and communicatively connected with a respiratory device 601 and an exercise device 602. The controller 50 includes at least one processor 501, and a memory 502 communicatively connected with the at least one processor 501, the memory 502 stores instructions executable by the at least one processor 501, and the memory 502 also stores the at least one physical rehabilitation strategy. The instructions, when executed by the at least one processor 501, cause the at least one processor 501 to: control at least one of a device setting of the respiratory device 601 and a device setting of the exercise device 602, based on a target physical rehabilitation strategy among the at least one physical rehabilitation strategy.

In a possible implementation, the instructions, when executed by the at least one processor 501, cause the at least one processor 501 to: receive a physiological parameter of the patient transmitted by at least one measurement device 603 associated with the patient; and adjust, based on the physiological parameter and the target physical rehabilitation strategy, the at least one of the device setting of the respiratory device 601 and the device setting of the exercise device 602.

In a possible implementation, the instructions, when executed by the at least one processor 501, cause the at least one processor 501 to: set the target physical rehabilitation strategy based on at least one input of a user, where the at least one input corresponds to a rehabilitation decision determined by the user.

In a possible implementation, the instructions, when executed by the at least one processor 501, cause the at least one processor 501 to: receive authentication information input by the user; and determine, according to the authentication information, whether the user has an authority for accessing the at least one physical rehabilitation strategy.

In a possible implementation, the instructions, when executed by the at least one processor 501, cause the at least one processor 501 to: output a reminder signal at a start time of the physical rehabilitation, where the start time of the physical rehabilitation is included in the target rehabilitation strategy, and the reminder signal is used to remind the patient that it is time for physical rehabilitation.

In a possible implementation, the system further includes a display screen 604 and a speaker 605 communicatively connected with the controller 50, and the instructions, when executed by the at least one processor 501, cause the at least one processor 501 to: output an exercise guidance for the physical rehabilitation through at least one of the display screen 604 and the speaker 605, where the exercise guidance is included in the target physical rehabilitation strategy and is used to provide a guidance for exercise to the patient.

In a possible implementation, the system further includes a camera 606 communicatively connected with the controller 50 and disposed in front of the patient, and the instructions, when executed by the at least one processor 501, cause the at least one processor 501 to: receive an image of the patient from the camera 606; and transmit the image of the patient to a remote terminal.

In a possible implementation, the system further includes an import device 607, such as a keyboard, which is connected with the controller 50 in a wired or wireless manner and can be used to import physical rehabilitation protocols (strategies) specific to an institution or a caregiver.

In a possible implementation, the system may be connected to cloud so that big data such as a duration of the physical rehabilitation for the patient to fully recover can be collected and analyzed to improve a physical rehabilitation strategy and to create an optimum physical rehabilitation strategy for a respiratory patient. The specific analysis algorithm may be an analysis algorithm in prior art, which is not limited in the embodiment of the present disclosure.

The system for assisting a patient in physical rehabilitation in the embodiment may perform the technical solutions of the method embodiments shown in FIG. 2 and FIG. 3, and the implementation principle and technical effects thereof are similar, and details are not described herein.

The present disclosure further provides a non-transitory computer readable storage medium, storing thereon computer executable instructions which, when being executed by a controller configurable with at least one physical rehabilitation strategy and communicatively connected with a respiratory device and an exercise, implement the method for assisting a patient in physical rehabilitation according to embodiments of the present disclosure.

The related description can be understood by referring to the related descriptions corresponding to FIG. 2 and FIG. 3, and details are not described herein.

Terms such as "first", "second" and the like in the specification and claims of the present disclosure as well as in the above drawings are intended to distinguish different objects, but not intended to define a particular order.

The term "a" or "an" is not intended to specify one or a single element, instead, it may be used to represent a plurality of elements where appropriate.

In one or more examples, the functions described may be implemented in hardware, software, firmware, or any combination thereof. For example, the functions may be implemented by one or more processors, such as one or more application specific integrated circuits (ASICs), field programmable logic arrays (FPGAs), or other equivalent integrated or discrete logic circuitry. Accordingly, the term "processor," as used herein may refer to any of the foregoing structure or any other structure suitable for implementation of the techniques described herein. In addition, the techniques could be fully implemented in one or more circuits or logic elements.

In the claims, the word "including" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate, preclude or suggest that a combination of these measures cannot be used to advantage.

The foregoing detailed description has been presented for purposes of illustration and description. It is not intended to be exhaustive or to limit the subject matter claimed herein to the precise form(s) disclosed. Many modifications and variations are possible in light of the above teachings. The described embodiments were chosen in order to best explain the principles of the disclosed technology and its practical application to thereby enable others skilled in the art to best utilize the technology in various embodiments and with various modifications as are suited to the particular use contemplated. Those embodiments with various modifications are within the range and scope of the following claims.

What is claimed is:

1. A method for assisting a person in physical exercise, wherein the method is executed by a controller configurable with at least one physical exercise strategy, the controller is communicatively connected with a respiratory device and an exercise device, and the method comprises:
controlling, based on a target physical exercise strategy among the at least one physical exercise strategy, at least one of a device setting of the respiratory device and a device setting of the exercise device.

2. The method according to claim 1, further comprising:
receiving a physiological parameter of the person transmitted by at least one measurement device associated with the person; and
adjusting, based on the physiological parameter and the target physical exercise strategy, the at least one of the device setting of the respiratory device and the device setting of the exercise device.

3. The method according to claim 2, wherein the physiological parameter comprises a heart rate of the person;
the adjusting, based on the physiological parameter and the target physical exercise strategy, the at least one of the device setting of the respiratory device and the device setting of the exercise device comprises:
determining whether the heart rate of the person exceeds an upper limit of a target heart rate range comprised in the target physical exercise strategy; and
when the heart rate of the person exceeds the upper limit of the target heart rate range, performing at least one of the following: modifying the device setting of the respiratory device to increase supplemental oxygen output by the respiratory device, or modifying the device setting of the exercise device to reduce an exercise intensity of the person.

4. The method according to claim 2, wherein the physiological parameter comprises SpO2 of the person;
the adjusting, based on the physiological parameter and the target physical exercise strategy, the at least one of the device setting of the respiratory device and the device setting of the exercise device comprises:
determining whether a value of the SpO2 is lower than a first preset threshold comprised in the target physical exercise strategy; and
when the value of the SpO2 is lower than the first preset threshold, performing at least one of the following: modifying the device setting of the respiratory device to increase supplemental oxygen output by the respiratory device, or modifying the device setting of the exercise device to reduce an exercise intensity of the person.

5. The method according to claim 4, wherein when the value of the SpO2 is lower than the first preset threshold, the method further comprises:
determining whether the value of the SpO2 is lower than a second preset threshold comprised in the target physical exercise strategy, wherein the second preset threshold is lower than the first preset threshold; and
outputting an alarm signal in a case that the SpO2 of the person is lower than the second preset threshold.

6. The method according to claim 1, wherein the controlling, based on a target physical exercise strategy among the at least one physical exercise strategy, at least one of a device setting of the respiratory device and a device setting of the exercise device comprises:
  determining whether the device setting of the respiratory device exceeds a third preset threshold, wherein the third preset threshold is comprised in the target physical exercise strategy; and
  modifying the device setting of the exercise device to reduce an exercise intensity of the person, in a case that the device setting of the respiratory device exceeds the third preset threshold.

7. The method according to claim 1, further comprising:
  setting the target physical exercise strategy based on at least one input of a user, wherein the at least one input corresponds to an exercise decision determined by the user.

8. The method according to claim 7, wherein before the setting the target physical exercise strategy based on at least one input of a user, the method further comprises:
  receiving authentication information input by the user; and
  determining, according to the authentication information, whether the user has an authority for accessing the at least one physical exercise strategy.

9. The method according to claim 1, further comprising:
  outputting a reminder signal at a start time of the physical exercise, wherein the start time is comprised in the target physical exercise strategy, and the reminder signal is used to remind the person that it is time for physical exercise.

10. The method according to claim 1, further comprising:
  receiving a stop instruction, wherein the stop instruction is input by the person by pressing a stop button on the controller, or the stop instruction is transmitted by the user through a remote terminal; and
  controlling the exercise device to stop running.

11. The method according to claim 1, further comprising:
  outputting an exercise guidance for the physical exercise through at least one of a display screen and a speaker, wherein the display and the speaker are communicatively connected with the controller, and the exercise guidance is comprised in the target physical exercise strategy and is used to provide a guidance for exercise to the person.

12. The method according to claim 1, further comprising:
  receiving an image of the person from a camera communicatively connected with the controller and disposed in front of the person; and
  transmitting the image of the person to a remote terminal.

13. A controller configurable with at least one physical exercise strategy and communicatively connected with a respiratory device and an exercise device, the controller comprising:
  at least one processor; and
  a memory communicatively connected with the at least one processor;
  wherein the memory stores instructions executable by the at least one processor, and the instructions, when executed by the at least one processor, cause the at least one processor to:
  control at least one of a device setting of the respiratory device and a device setting of the exercise device, based on a target physical exercise strategy among the at least one physical exercise strategy.

14. A system for assisting a person in physical exercise, comprising a controller configurable with at least one physical exercise strategy and communicatively connected with a respiratory device and an exercise device;
  wherein the controller comprises at least one processor, and a memory communicatively connected with the at least one processor, the memory stores instructions executable by the at least one processor, and the instructions, when executed by the at least one processor, cause the at least one processor to:
  control at least one of a device setting of the respiratory device and a device setting of the exercise device, based on a target physical exercise strategy among the at least one physical exercise strategy.

15. The system according to claim 14, wherein the instructions, when executed by the at least one processor, cause the at least one processor to:
  receive a physiological parameter of the person transmitted by at least one measurement device associated with the person; and
  adjust, based on the physiological parameter and the target physical exercise strategy, the at least one of the device setting of the respiratory device and the device setting of the exercise device.

16. The system according to claim 14, wherein the instructions, when executed by the at least one processor, cause the at least one processor to:
  set the target physical exercise strategy based on at least one input of a user, wherein the at least one input corresponds to an exercise decision determined by the user.

17. The system according to claim 16, wherein the instructions, when executed by the at least one processor, cause the at least one processor to:
  receive authentication information input by the user; and
  determine, according to the authentication information, whether the user has an authority for accessing the at least one physical exercise strategy.

18. The system according to claim 14, wherein the instructions, when executed by the at least one processor, cause the at least one processor to:
  output a reminder signal at a start time of the physical exercise, wherein the start time of the physical exercise is comprised in the target physical exercise strategy, and the reminder signal is used to remind the person that it is time for physical exercise.

19. The system according to claim 14, further comprising a display screen and a speaker communicatively connected with the controller,
  wherein the instructions, when executed by the at least one processor, cause the at least one processor to:
  output an exercise guidance for the physical exercise through at least one of the display screen and the speaker, wherein the exercise guidance is comprised in the target physical exercise strategy and is used to provide a guidance for exercise to the person.

20. The system according to claim 14, further comprising a camera communicatively connected with the controller and disposed in front of the person;
  wherein the instructions, when executed by the at least one processor, cause the at least one processor to:
  receive an image of the person from the camera; and
  transmit the image of the person to a remote terminal.

* * * * *